United States Patent [19]

Allen

[11] 4,242,242

[45] Dec. 30, 1980

[54] HIGHLY ABSORBENT FIBERS OF RAYON WITH SULFONIC ACID POLYMER INCORPORATED

[75] Inventor: Thomas C. Allen, Asheville, N.C.

[73] Assignee: Akzona Incorporated, Asheville, N.C.

[21] Appl. No.: 805,361

[22] Filed: Jun. 10, 1977

[51] Int. Cl.³ ................................................ C08L 1/02
[52] U.S. Cl. ........................... 260/17.4 CL; 128/284; 128/285; 264/192
[58] Field of Search ................................. 260/17.4 CL

[56] References Cited

U.S. PATENT DOCUMENTS

| | | | |
|---|---|---|---|
| 3,213,053 | 10/1965 | Kendrick | 260/29.6 RB |
| 3,708,446 | 1/1973 | Pettitt | 260/17.4 |
| 3,709,780 | 1/1973 | Slagel et al. | 260/17.4 GC |
| 3,770,673 | 11/1973 | Slagel et al. | 260/17.4 GC |
| 3,826,767 | 7/1974 | Hoover et al. | 260/17.4 GC |
| 3,929,740 | 12/1975 | Englehardt et al. | 525/366 |
| 3,951,889 | 4/1976 | Smith | 260/17.4 |
| 4,028,290 | 6/1977 | Reid | 260/17.4 GC |
| 4,051,086 | 9/1977 | Reid | 260/17.4 |
| 4,066,584 | 1/1978 | Allen et al. | 260/17.4 CL |
| 4,076,663 | 2/1978 | Masuda et al. | 260/17.4 GC |
| 4,104,214 | 8/1978 | Meirhoefer | 260/17.4 |
| 4,134,863 | 1/1979 | Fanta et al. | 260/17.4 GC |

*Primary Examiner*—Edward M. Woodberry
*Attorney, Agent, or Firm*—Francis W. Young; Jack H. Hall

[57] ABSTRACT

Highly absorbent cellulosic fibers are made by incorporating therein from 2%–35% based on the weight of cellulose of a polymerized acrylamido-2-methylpropane sulfonic acid or a copolymer of acrylamido-2-methylpropane sulfonic acid with any one or combination of other polymerizable hydrophilic monomers such as acrylic acid, methacrylic acid, acrylonitrile and the like.

29 Claims, No Drawings

HIGHLY ABSORBENT FIBERS OF RAYON WITH SULFONIC ACID POLYMER INCORPORATED

BACKGROUND OF THE INVENTION

This invention relates to highly absorbent fiber, for example, viscose rayon, hydroxypropylcellulose, and hydroxyethylcellulose, made from wood pulp or other cellulosic materials, which are useful in the production of nonwoven articles such as diapers, tampons, sanitary napkins, medical sponges, soil mulches, wiping cloths, and the like. Each of these applications requires a material having a high capacity for absorbing and retaining water and other aqueous fluids, particularly body fluids. Cellulosic fibers have found wide use in these and similar applications because of the hydrophilic nature of the cellulose molecule and the fibrous structure which contributes integrity, form, shape, wicking ability, and liquid retention to a nonwoven material.

Some examples of attempts to increase the absorbency of rayon fibers can be found in such techniques as U.S. Pat. No. 3,419,345 to Parrish in which rayon fibers are neutralized with a sulfate solution; and, U.S. Pat. No. 3,525,735 to Miller, in which alkali cellulose is reacted with an etherifying agent comprising acrylonitrile. In fact, the incorporation of additive material in viscose to modify the absorbency of the resulting rayon product is known in the art. As examples only, attention is called to U.S. Pat. No. 3,423,167 to Kuzmak et al., 3,847,636 to Smith, and U.S. Pat. No. 3,525,735 to Miller, which teach the incorporation into viscose of carboxymethylcellulose and carboxyethylstarch and acrylonitrile respectively, to increase the hydrophilic properties of the fiber. Typically, for maximum absorbency, the additive is in a salt form in the fiber, as in U.S. Pat. No. 3,844,287 to Smith in which the additive is the alkali metal and ammonium salt of polyacrylic acid.

The instant invention is directed to the incorporation of additive material of a structure not suggested by the prior art. The essential monomer used with this invention is described in detail in U.S. Pat. No. 3,506,707 to Miller et al.

SUMMARY OF THE INVENTION

To obtain rayon fibers of greatly enhanced absorbency, alkali metal and ammonium salts of polymers or copolymers of 2-acrylamido-2-methylpropane sulfonic acid are incorporated throughout the fibers. The invention embraces the addition of at least about 2% of the polymer to the cellulose, based on the weight of cellulose, and the concentration can be as high as 35% or greater, but the preferred range, based on efficiency, retention and economic considerations is 5–15%.

Copolymers of particular interest for enhanced absorbency are those of varying ratios of the sulfonic acid monomer with acrylic acid, methacrylic acid or acrylonitrile. Other comonomers are also suitable, such as:
acrylamide
methacrylamide
itaconic acid
crotonic acid
maleic acid
hydroxyethyl acrylate
hydroxyethyl methacrylate
hydroxypropyl acrylate
hydroxypropyl methacrylate
allyl alcohol
ethoxyethyl acrylate
ethoxyethyl methacrylate and
vinyl sulfonic acid Molecular weights of the preferred embodiments have not been precisely determined, but the order of magnitude of 50,000 to 1,000,000, is preferred. Any molecular weight in the range considered to be a polymer is considered consistent with the instant invention, although adjustments to fit particular practical conditions may be necessary.

Water absorption of a material depends upon the degree of hydrophilicity it exhibits. Such determinations of water absorption as those based upon swelling observed and water retention observed under centrifugation are considered dependent on the degree of ionization of the material. Hence, the more strongly acidic a material is which is incorporated in a fiber, the more absorptive it can be expected to be.

Sulfonic acid groups employed in accordance with this invention are particularly useful for this purpose because of their extremely high hydrophilic properties and their ability to hydrogen bond with water. Marked increase in the absorbency of rayon fibers has been realized by incorporation of sulfonic acid group-containing polymers in accordance with this invention.

Polymerization of additional different monomers with the sulfonic acid monomer alone or with other heterogeneous monomers is contemplated to incorporate sites which accomplish various objectives. Generally, from at least 10 percent to about 90 percent by weight of such a copolymer should be the sulfonic acid monomer. A range of weight ratios from 35:65 to 70:30 of AMPS:Comonomer is preferred. The copolymer with acrylamide, acrylonitrile, acrylic acid or methacrylic acid, can be considered to be such an addition product to reduce the cost of the basic essential polymer by reacting the monomer with a complementary material which is less expensive. Another application would be incorporation of a site which reacts with cellulose or other functional groups in the copolymer so as to insolubilize the polymer to thereby retain a higher amount in the fiber, a good example of such additive monomer being N-methylolacrylamide.

These and other objects, features, advantages, and characteristics of the invention will be more apparent upon consideration of the following detailed descriptions of preferred embodiments of the invention.

DETAILED DESCRIPTION OF THE INVENTION

This invention is accomplished by adding polymers or copolymers of 2-acrylamido-2-methylpropane sulfonic acid (AMPS$^{TM}$-AMPS is a trademark of the Lubrizol Corporation, P. O. Box 3057, Cleveland, Ohio 44117) to a typical viscose solution; allowing these polymers or copolymers to intermix with the sodium cellulose dithiocarbonate molecules in solution; and, then precipitating the mixed polymer in the normal viscose rayon spinning process.

Fibers described in the following preferred embodiments were manufactured by injecting solutions of the sulfonic acid polymers and copolymers of their partial or completely neutralized salts, into viscose solutions, followed by formation of rayon filament fibers by extruding the viscose through spinneret openings into an acid bath.

The fibers of the invention can be prepared by adding, at any stage of viscose aging, but preferably by injecting into the fully ripened viscose solution, an amount of polymer or copolymer in the range of 2 to about 35% by weight, based on the weight of cellulose in the viscose solution (hereafter all percentages are given on this basis and referred to as CIV). We prefer the range of 5-15% CIV, based on a balance between increasing absorbency, economic factors, and processing conditions.

The viscose solution may be prepared by conventional steps. This may include steeping conventional chemical cellulose sheet prepared from wood pulp or cotton linters in a caustic soda solution (NaOH) and thereafter removing caustic soda by pressing or the like to the desired solids content. The resulting alkali cellulose is shredded and, after aging, is mixed with carbon disulfide to form an aqueous alkaline xanthate (viscose) solution. For best results, the concentrations of the viscose solution are from about 5 to 10 percent by weight cellulose, from about 4 to 8 percent by weight sodium hydroxide, sufficient carbon disulfide to provide from about 1.7 to 3.0 percent sulfur and the remainder water. In each of the examples given hereinafter to illustrate the invention, the viscose solution contains from about 8.0 to 9.0 percent by weight cellulose, from about 4.5 to 5.5 percent by weight sodium hydroxide, carbon disulfide to provide from about 2.2 to 2.5 percent sulfur and the remainder water.

The viscose solution containing the polymer or copolymer is then spun or extruded through spinneret openings into an acid bath where the cellulose fiber is regenerated. The regenerated fiber is stretched in air from 0-100%, or even higher, if desired, preferably from about 30 to 50% and then run through a hot aqueous bath which can be maintained at a temperature of from ambient to 100° C., preferably from 90°-97° C. The hot aqueous bath contains various amounts of dilute sulfuric acid, $ZnSO_4$ and sodium sulfate. The fiber is subjected to a second stretching of from 0 to 100% in the hot bath. The total stretch in both steps is preferably in the range of 50-70%. The stretching, as is well known, imparts the necessary strength to the finished fiber. The fibers, now a large bundle of continuous filaments or tow, from the combined output of a number of spinnerets are cut into short fibers of any desired length and washed and dried to a moisture content of around 11% and baled.

Depending upon the spinning conditions, after the fiber is regenerated in the acid bath, the polymer or copolymer occluded in the fiber may be in acid form or alkali metal or ammonium salt form or a combination thereof. However, the homopolymer or copolymer should be in the form of the alkali metal or ammonium salt in order to achieve the highest degree of absorbency. Complete conversion to the salt form can occur during an alkaline sodium sulfide wash bath which is conventionally used to remove metal and sulfur impurities. In some instances, it may be desirable, particularly, if an acid wash follows the sulfide, to treat the fiber with a base such as a dilute solution of sodium bicarbonate, sodium hydroxide, and the like, to complete the conversion, and insure that a high percentage of the copolymer is in the salt form. It may be necessary to limit the amount of conversion to the salt form for certain applications where the material may come into contact with the body, since a pH which is much higher than 7 to 7.5 can cause irritation of delicate membranes and serves to promote the growth of harmful microorganisms. Finally, a conventional finish, such as a surfactant, may be applied and the staple fiber is dried in a continuous drier to a predetermined moisture content suited to the particular end use of the fiber.

The fiber can then be baled or carded for processing into one of the final products mentioned previously. A particularly suitable use for the fiber of the invention is for tampons, which may be made, for example, by one of the methods referred to in U.S. Pat. No. 3,699,965, or by other well-known methods.

In the following examples solutions of the polymers and copolymers or their partial sodium salts, are injected into the viscose solutions and rayon fibers are formed by standard machines and processes as described in the above.

EXAMPLE 1

The acid spin bath used to coagulate and regenerate the cellulose of the Samples below contained 8.5% sulfuric acid, 5.0% of $Mg SO_4$, 3.0% of $Zn SO_4$, 18.2% of $Na_2 SO_4$ and 30-35 ppm laurylpyridinium chloride (LPC) at 49°-51° C. and gave an 1100 denier yarn containing 480 filaments. The resulting yarn was then run through a fresh hot water bath at 93°-95° C. and stretched 37% in the bath. The yarn was then collected in a pot in cake form, washed at 30° C. for 40 minutes at 52° C. in 0.50% aqueous sodium sulfide containing 0.05-0.10 sodium hydroxide, for 80 minutes at 30° C. in water, for 40 minutes at 30° C. in 0.01% acetic acid, for 40 minutes at 40° C. in 0.2% solution of an emulsified mineral oil controlled to a pH of 7 to 8, hydroextracted for 4.5 minutes, and dried at 70°-80° C. overnight.

After the fiber is regenerated in the acid bath, the additive in the fiber will be in acid form. The additive should be in the alkali-metal or ammonium salt form to achieve maximum absorbency. This conversion occurs during the alkaline sodium sulfide wash bath (or the equivalent) which is conventionally used to remove metal and sulfur impurities.

Sample A—5 parts by weight with respect to 100 parts of the weight of the cellulose of partial sodium salts of 2-acrylamido-2-methylpropane sulfonic acid of molecular weight of approximately 500,000 are added to the viscose solution and the fibers are manufactured as described.

Sample B—5 parts by weight with respect to 100 parts of the weight of the cellulose of partial sodium salts of a hydrolyzed copolymer of 65 parts by weight acrylonitrile and 35 parts by weight 2-acrylamido-2-methylpropane sulfonic acid of molecular weight of approximately in the range of 200,000 to 300,000 are added to the viscose solution and the fibers are manufactured as described. The hydrolysis was accomplished by contacting the AMPS-acrylonitrile copolymer with aqueous sodium hydroxide by conventional hydrolysis procedures to convert the nitrile groups to a mixture of amide and sodium carboxylate groups.

Samples C—As a control sample, fibers are manufactured in the same manner from a viscose solution identical to that used to prepare samples A and B, with none of the subject additives.

EXAMPLE 2

The samples of Example 2 are similar to Example 1, except that they are manufactured with staple fiber equipment, rather than filament equipment.

A solution of the additive polymer or copolymer was partially neutralized to a pH of 5.2 before injecting into a viscose solution at a concentration of 10% CIV, thoroughly mixed with the viscose and spun into a conventional acid spinbath containing about 5% sulfuric acid, about 20% sodium sulfate, about 1% zinc sulfate and 25 ppm laurylpyridinium chloride at 56°–58° C. to coagulate and regenerate the cellulose to give a 22,448 denier fiber tow containing 7,496 filaments. The resulting tow was stretched 40% in air, run through a second bath at 92°–97° C. containing 3.2% sulfuric acid and about 6.15% total salts ($NaSO_4 + ZnSO_4$) and stretched 18% in the bath. The two was then cut into 1 9/16″ staple fiber lengths. The stable was then washed with water, then with 0.30% sodium sulfide solution, followed with water, then with a 0.175% sulfuric acid solution, followed with water, and then followed by a 0.20% sodium bicarbonate wash. A finish solution consisting of a 0.30% aqueous solution of ethoxylated sorbitan monooleate and ethoxylated stearic acid was applied before the fibers were dried for about ½ hour in a continuous oven set at about 80° C., for about ½ hour at about 70° C., and for about another ½ hour at about 50° C. The final moisture content was about 11%.

Sample D—5 parts by weight with respect to 100 parts of the weight of cellulose of partial sodium salts of a hydrolyzed copolymer of 65 parts by weight of acrylonitrile and 35 parts by weight 2-acrylamido-2-methylpropane sulfonic acid of molecular weight approximately in the range of 200,000 to 300,000 are added to the viscose solution and the fibers are manufactured as described.

Sample E—As a control sample, fibers are manufactured in the same manner from a viscose solution with none of the subject additives.

Sample F—As a comparison sample, fibers are manufactured in essentially the same manner from a viscose solution but incorporating 5 parts by weight with respect to 100 parts of the weight of cellulose of alkali metal and ammonium salts of polyacrylic acid in accordance with U.S. Application Ser. No. 330,378, filed Feb. 7, 1973 and U.S. Pat. No. 3,844,287 to Smith.

EXAMPLE 3

Sample G—10 parts by weight with respect to 100 parts of the weight of the cellulose in the viscose is added by adding a 30% wt. solution of the sodium salt of a polymer of 2-acrylamido-2-methylpropane sulfonic acid having a Brookfield viscosity (#2 spindle/6 rpm) at 25° C. of 1,150 cps. and an inherent viscosity of 1.05 at 0.5% wt. polymer in 3% wt. aqueous NaCl at 30° C. was added to the viscose solution and fibers produced as in Example 2.

Sample H—Sample G was repeated except 15 parts by weight of the polymer was added to the viscose.

Sample I—As a control sample, the fibers are made with no polymer added.

EXAMPLE 4

This example illustrates the effect of an AMPS copolymer with acrylic acid on the properties of the fiber.

Sample J—10 parts by weight with respect to 100 parts of the weight of the cellulose in the viscose is added by adding a 20% wt. solution of the sodium salt of a 70/30 wt/wt copolymer of 2-acrylamido-2-methylpropane sulfonic acid/acrylic acid having a Brookfield viscosity (#2 spindle/6 rpm) at 25° C. of 850 cps. and an inherent viscosity of 1.03 at 0.5% wt. copolymer in 3% wt. aqueous NaCl at 30° C. was added to the viscose solution and fibers produced as in Example 2.

Sample K—Sample J was repeated except 15 parts by weight of the polymer was added to the viscose.

Sample L—As a control sample, the fibers are made with no polymer added.

Sample M—As a further control, Sample J was repeated except a 27.5% solution of the partial sodium salt of polyacrylic acid (partially neutralized Acrysol A-3 from Rohm & Haas Co.) having a Brookfield viscosity of about 3500 cps. and a viscosity average molecular weight of approximately 150,000 was added to the viscose.

Sample N—Sample K was repeated except the polymer solution from Sample M was added to the viscose.

EXAMPLE 5

Sample O—10 parts by weight with respect to 100 parts of weight of the cellulose in the viscose of a 67/33 wt. of a partially neutralized copolymer of AMPS/methacrylic acid having a Brookfield viscosity (#2 spindle/6 rpm) at 25° C. of 1,950 cps. and an inherent viscosity of 1.24 at 0.5% wt. polymer in 3% wt. aqueous NaCl at 30° C. was added to the viscose solution and fibers produced as in Example 2.

Sample P—Sample O was repeated except 15 parts by weight of the polymer was added to the viscose.

Sample Q—As a control sample the fibers are made with no polymer added.

EXAMPLE 6

Sample R—Is a terpolymer of 45% by weight 2-acrylamide-2-methylpropane sulfonic acid (AMPS), 55% by weight methacrylic acid (MAA), and 5% by weight N-methyol acrylamide (NMA).

Sample S—Is a copolymer of 50% by weight AMPS and 50% by MAA.

Preparation of these polymers was in accordance with the description below under the major heading "Polymer Preparation" and under the subheading "Preparation of 50:50 by weight AMPS-Na/Sodium Methacrylate."

TESTS CONDUCTED

Centrifuge Water Retention

The degree of selling of rayon, "Q", is defined as the ratio of the weight of water contained in the swollen yarn, after the water which is mechanically held among the fibers has been eliminated by centrifugal force, to the bone-dry weight of the rayon. Two kinds of swelling may be distinguished: Primary Swelling, which is that of rayon which has never been dried; and Secondary Swelling, which is that of rayon which has been washed and dried, and then thoroughly re-wet.

Special Equipment

1. Centrifuge

The centrifuge consists of a solid aluminum head, mounted on a spinning pot motor. Four cavities in the head are designed to contain the sample holders and also the water extracted from the rayon sample. The synchronous motor, running at 7900 r.p.m., develops a relative centrifugal force of 2000 to 3500 times gravity, depending upon whether the radius is measured at the top of the sample cup (ca. 3.0 cm) or at the perforated bottom of the cup (ca. 5.0 cm). This force is well above the level at which substantial variations will cause measurable differences in the amount of water extracted.

2. Sample Holders

The stainless steel sample holders are cylindrical cups (22 mm I.D.×25 mm deep) with perforated bottoms. Screw caps are provided to cover both ends. The cups and ends are numbered to prevent interchange of parts.

Procedure

For the secondary swelling or water retention value, dried fibers are placed in a beaker of distilled water until thoroughly saturated.

A portion of the prepared sample (equivalent to about 2.5 g. dry rayon) is placed in a sample holder, which has been previously weighed together with both caps. The holder is closed with the top cap (to prevent drying of the rayon) and placed in the centrifuge. (Sample holders are always placed in pairs in opposition positions in the centrifuge head).

The motion is started and the sample is centrifuged for 1 to 2 minutes. Then the centrifuge is stopped, the sample holder removed, and the water then extracted by pipet from the cavity in the head.

The sample holder is returned to the centrifuge and spun for 15 minutes. The holder is removed and wiped with a dry cloth. The cap is placed on the bottom, and the holder containing the extracted rayon is weighed.

The damp rayon is placed in a previously weighed weighing bottle and dried overnight in the oven at 105° C. After drying, the bottle is removed, the cap is closed, and it is allowed to cool. The bottle and the dry rayon are weighed.

Calculation

Swollen Weight—(weight of yarn+holder)—(-weight of holder)

Bone Dry Weight—(weight of dry yarn+bottle)—weight of bottle)

Degree of Swelling ("Q")=(Swollen Weight−Bone Dry Weight)/Bone Dry Weight

Syngyna Absorbency

Samples in accordance with this invention were transmitted to an established tampon manufacturer which cooperated by performing its usual syngyna absorbency tests and reporting the results back. The syngyna absorbency test is generally known in the art and has been described in a paper by G. W. Rapp, Professor of Biochemistry and Physiology, Loyola University, Chicago, Illinois, entitled "A comparison of the Absorptive Efficiency of Commercial Catamenial Tampons."

The test equipment comprises a glass tubular shell with a side tubular inlet and an end tubular inlet. The end of the tube opposite the end inlet is large enough to receive the tampon or the like to be tested. A disposable rubber tube is sealed around the tampon receiving end and extends across the tube. Conduits from a test-liquid source extend from the tubular inlet and pierce the rubber tube.

Water to provide a pressure head is applied through the side tubular inlet which fills the glass tube (around the rubber tube) and presses the rubber tube against a tampon or the like inserted in the center of the rubber tube. Liquid from the test-liquid source is dripped through the conduit on to the tampon or the like, at a rate such that the liquid is not allowed to pool near the outlet in the glass tube.

The object of the test is to determine the maximum absorbency of the material in the glass tube. The test is terminated when the first drop of test liquid is seen dripping from the end of the material being tested. Results may be expressed in total weight of test liquid absorbed, in which case the amount of material being tested is held standard, or the results may be expressed as the ratio of the weight of test liquid absorbed to the weight of the material tested (g/g).

In the syngyina absorbency tests reported herein, the test liquid was a mixture of 60 parts by volume human blood to 40 parts by volume water.

Demand Wettability

The so-called Demand Wettability Test (Lichstein, Bernard, International Nonwovens and Disposables Association, 2nd Annual Symposium on Non-woven Product Development, Mar. 5–6, 1974, Washington, D.C.), uses a novel apparatus which allows the measure of volume and rate of absorption of a fluid by maintaining the absorbent material at a zero hydrostatic head so that wetting occurs purely on demand by the absorbent material. Thus, the absorption of liquid occurs only by virtue of the ability of the absorbent material to demand liquid, with the flow of liquid abruptly stopping at the point of saturation.

In the tests conducted, the compressed results simulate a tampon test. Compression was accomplished by pressing one gram of fiber in a one-inch diameter cylinder to a pellet of approximately one-eighth inch thickness using a pressure of 10,000 p.s.i. on a 6-inch ram.

The uncompressed results simulate a diaper or sanitary napkin application.

TEST RESULTS

TABLE I

| SAMPLE | POLYMER INCORPORATED | CENTRIFUGE WATER RETENTION |
|--------|----------------------|----------------------------|
| C | None | 0.96 |
| A | 100% AMPS 5% on wt. of cellulose | 1.24 |
| B | 65/35 Hydrolyzed Acrylonitrile/AMPS Copolymer 5% on wt. of cellulose | 1.27 |

TABLE II

| SAMPLE | POLYMER INCORPORATED | CENTRIFUGE WATER RETENTION | CENTRIFUGE SALINE RETENTION |
|--------|----------------------|------------------------------|-------------------------------|
| E | None | 0.79 | — |
| D | 5% on weight of cellulose of 65/35 Hydrolyzed Copolymer of Acrylonitrile/AMPS | 1.04 | — |

TABLE III

| SAMPLE | POLYMER INCORPORATED | SYNGYNA ABSORBENCY Total Gms.* | g/g* |
|--------|----------------------|--------------------------------|------|
| E | None | 15.69 | 4.49 |
| D | 5% on wt. of cellulose of Hydrolyzed 65/35 | 19.69 | 5.69 |

TABLE III-continued

| SAMPLE | POLYMER INCORPORATED | SYNGYNA ABSORBENCY Total Gms.* | g/g* |
|---|---|---|---|
| | Copolymer of Acrylonitrile/AMPS | | |

*Average of ten samples

TABLE IV

| SAMPLE | POLYMER INCORPORATED | DEMAND WETTABILITY* Uncompressed Saline' 0.1 psi | DEMAND WETTABILITY* Uncompressed Saline' 0.2 psi | Compressed Saline ml/g |
|---|---|---|---|---|
| E | None | 16.9 | 15.8 | 4.2 |
| F | 5% Polyacrylic Acid | 18.3 | 16.4 | 6.7 |
| D | 5% of hydrolyzed 65/35 copolymer of AMPS/Acrylonitrile | 19.5 | 17.5 | 7.0 |

*Average of three trials
'1% NaCl in distilled water

TABLE V

| SAMPLE | POLYMER INCORPORATED | FIBER pH | CENTRIFUGE RETENTION VALUES | VALUES SALINE g/g | SYNGYNA ABSORBENCY g/g | DEMAND WETTABILITY SALINE COMPRESSED g/g |
|---|---|---|---|---|---|---|
| G | 10% AMPS | 7.7 | 1.15 | 1.02 | 5.77 | 6.7 |
| H | 15% AMPS | 8.4 | 1.31 | 1.20 | 6.14 | 7.0 |
| I | None | 7.6 | 0.79 | 0.76 | 4.72 | 6.0 |

TABLE VI

| SAMPLE | POLYMER INCORPORATED | FIBER pH | CENTRIFUGE RETENTION VALUES WATER g/g | CENTRIFUGE RETENTION VALUES SALINE g/g | SYNGYNA ABSORBENCY g/g | DEMAND WETTABILITY g/g |
|---|---|---|---|---|---|---|
| J | 10% 70/30 AMPS/Acrylic Acid | 8.5 | 1.32 | 1.13 | 6.12 | 7.1 |
| K | 15% 70/30 AMPS/Acrylic Acid | 8.9 | 1.44 | 1.23 | 6.33 | 7.1 |
| L | None | 7.6 | 0.79 | 0.76 | 4.72 | 6.0 |
| M | 10% Poly-Acrylic Acid | 7.6 | 1.18 | 1.02 | 5.82 | 6.7 |
| N | 15% Poly-Acrylic Acid | 8.2 | 1.47 | 1.28 | 6.29 | — |

TABLE VII

| SAMPLE | POLYMER INCORPORATED | FIBER pH | CENTRIFUGE RENTENTION VALUES WATER g/g | CENTRIFUGE RENTENTION VALUES SALINE g/g | SYNGYNA ABSORBENCY g/g | DEMAND WETTABILITY SALINE COMPRESSED g/g |
|---|---|---|---|---|---|---|
| O | 10% 67/33 AMPS/Methacrylic Acid | 8.6 | 1.20 | 1.07 | — | — |
| P | 15% 67/33 AMPS/Methacrylic Acid | 8.2 | 1.42 | 1.23 | — | — |
| Q | None | 7.6 | 0.79 | 0.76 | — | — |

SOME ANALYSIS

It should be pointed out that while equal weight amounts of polyacrylic acid in Samples M and N of Example 4 (reported in Table VI) compared to the copolymer Samples J and K, and the homopolymer Samples G, H, and I of Example 3, the molecular weight of AMPS is approximately 3 times the molecular weight of acrylic acid, giving fewer sulfonic acid groups than carboxylic acid groups. Thus, if 10% wt. polyacrylic acid is added to the viscose as in Sample M, there exists 1.39 milliequivalents of acrylic acid per part of cellulose. In the case of the 70/30 wt/wt copolymer of AMPS/acrylic acid in Sample J, in a corresponding 10% by weight addition there exists 0.76 milliequivalents of acid total or 0.34 milliequivalents of AMPS per part of cellulose and 0.42 milliequivalents of acrylic acid per part of cellulose. In the case of the AMPS homopolymer in Sample G of Example 3, there exists 0.48 milliequivalents of AMPS per part of cellulose. In the case of 15% wt. of the various polymers added, there exists the following number of milliequivalents of monomer per part of cellulose:

Acrylic Acid (Sample N): 2.08

70/30 AMPS/Acrylic Acid (Sample K): 0.51 AMPS & 0.62 Acrylic Acid

AMPS (Sample H, Example 3): 0.72

When the results in Table VI are examined in view of the number of milliequivalents present, the greater absorbency imparted by the AMPS unit is seen more clearly.

GENERAL CONSIDERATIONS

The sodium salt of the 2-acrylamido-2-methylpropane sulfonic acid monomer, a 25% solution of the polymer of the sodium salt of that sulfonic acid, and a 25% solution of the polymer of that sulfonic acid prepared in free acid form have been reported privately by a reputable supplier as having been assayed by an independent laboratory and found to be non-toxic orally, non-irritating to the eye, and non-irritating to the skin within the meaning to the Federal Hazardous Substances Labeling Act.

The use of comonomers with the sulfonic acid containing monomers is particularly important since varying objectives can be accomplished. Use of complementing hydrophilic groups can reduce the cost of the polymer. An example is the use of acrylonitrile in the copolymer examples above since acrylonitrile is the starting material for 2-acrylamido-2-methylpropane sulfonic acid and consequently is much cheaper.

Comonomers are useful to accomplish other objectives such as to react with cellulose or other functional groups in the copolymer or in added materials so as to insolubilize the copolymers to thereby retain a higher amount in the fiber. Such comonomers contemplated include N-methylol acrylamide, hydroxymethyl diacetone acrylamide, glycidyl methacrylate, hydroxyethyl acrylate, hydroxyethyl methacrylate, hydroxypropyl acrylate hydroxypropyl methacrylate, and acrylamide. (Of course, in certain applications some monomers must be avoided because they are toxic or otherwise incompatible in the specific application). It is expected that a terpolymer of acrylonitrile, 2-acrylamido-2-methylpropane sulfonic acid, and N-methylol acrylamide will react with cellulose to retain a higher amount of copolymer.

The polymers of Example 6 were made as illustrative of the property of reactivity of a comonomer to insolubilize the polymer. The two materials of Example 6 showed polymer retention after water extraction as follows:

TABLE VIII

| POLYMERS | % EXTRACTABLE SOXHLET WATER 24 HOURS |
|---|---|
| Sample O - 45 AMPS/55 MAA/5 NMA | 1.3 |
| Sample R - 50 AMPS/50 MAA | 4.99 |

POLYMER PREPARATION

All polymers and copolymers employed in the foregoing examples were prepared and supplied as such by the Lubrizol Corporation.

That company makes generally available the following information with respect to procedures to prepare AMPS polymers and copolymers.

Polymerization Recipes

The following recipes are given as a guide to the homopolymerization and copolymerization of AMPS monomer and its sodium salt. The polymerizations, except where noted otherwise, should be conducted in a resin flask equipped with a stirrer, gas inlet tube, condenser and thermometer. All solutions should be purged for one hour with nitrogen or argon before adding the initiator, with purging continued during the polymerizations. All amounts are in grams.

Homopolymerization

AMPS Monomer—100
Distilled Water—100
Ferrous Sulfate Heptahydrate—0.01
Hydrogen Peroxide 0.05% Solution—0.25

Prepare a solution of AMPS monomer in water in a 800 ml beaker. Purge. Add the ferrous sulfate and hydrogen peroxide. The solution gels almost instantly. The temperature rises to 75°–80° C. in about two minutes. Cool to room temperature. Cut gel into pieces and dry at 60° in a vacuum oven.

Solution Copolymerization of the Sodium Salt of AMPS Monomer with Acrylamide AMPS Monomer—40.7
Sodium Hydroxide—7.85
Distilled Water—75.0
Acrylamide—5.0
Sodium Lauryl Sulfate—0.75
Sodium Meta-Bisulfite—0.0015
Ammonium Persulfate—0.003
Benzene, C.P.—500

Dissolve the sodium hydroxide with stirring in water. Cool in an ice bath, and add AMPS monomer at 25° C. (Maximum). Adjust pH to 8 with 20% sodium hydroxide solution. Add acrylamide. Purge. Add sodium lauryl sulfate. Add ammonium persulfate. Add sodium meta-bisulfite. Add benzene which has been purged previously. Heat to 50° C. and hold at 50° C. for 3.5 hours. Remove the water by azeotropic distillation. Remove the benzene by decantation and dry the polymer.

Slurry Copolymerization of AMPS Monomer with Acrylonitrile

AMPS Monomer—5.0
Acrylonitrile—45.0
Distilled Water—1000.0
Ferrous Sulfate Heptahydrate—0.15
Hydrogen Peroxide—0.05

Prepare a solution of the monomers with stirring in water. Purge. Add ferrous sulfate. Add hydrogen peroxide. After 8 hours, filter, wash the precipitate with water and dry.

The Lubrizol Corporation has supplied the following procedures as representative of those employed in making the polymers and copolymers used in the foregoing examples.

Preparation of AMPS-Na Polymer

Monomer Solution Preparation

Materials:

I. Compressed air
II. Water-deionized or distilled—8,000 g
III. Sodium hydroxide—1,050 g
IV. AMPS-reaction grade—5,424 g Procedure 1. Dissolve III in II.

2. Cool to 25° C. While stirring and purging below the surface with I, add IV, keeping the temperature at 25°-40° C.

3. Stir this solution at room temperature for 60 minutes or more, (at pH 9.0) purging with I.

4. Adjust the pH of the solution to 9.0 with 20% w aqueous AMPS solution.

5. Adjust the solution weight to 15,000 g with water.

6. Pressure filter the solution to remove precipitated iron and other insolubles. This gives a 40% w AMPS-Na solution.

Polymerization

Materials:

V. AMPS-Na solution 40% w—12,486 g
VI. Water-deionized—3,961 g
VII. Purified nitrogen
VIII. Sodium metabisulfite*—4.14 g
IX. Ammonium persulfate*—9.95*

*Since the quality of the AMPS monomer and AMPS-Na solutions prepared from it varies, the amount of initiator (VIII/IX) necessary to give a polymer of the desired viscosity may differ from one batch to another. Therefore, a small pilot experiment should be run with each batch of AMPS-Na monomer solution to determine the initiator level before proceeding on a large scale.

Procedure

1. A 5-gal glass reactor, equipped with a stainless steel paddle stirrer, gas inlet tube, thermometer and condenser was charged with V and VI.

2. Stirred and heated to 40° C., purging below the surface with VII at 1.0 SCFH.

3. Stirred at 40° C., purging with VII at 1 SCFH for an additional 30 minutes.

4. Applied an ice water cooling bath to the outside of the reactor and added VIII and IX (each dissolved in 100 g of water). The temperature rose from 40° to 67° in 5 minutes. The ice bath was lowered and the mixture stirred at 65°-68° under nitrogen for 1 hour.

5. Cooled to room temperature.

6. Mixed with 8,378 g water. This gives a 20% w solution of the product.

7. Determined Brookfield viscosity using number 2 spindle at 6 rpm. It was 1300 cp.

Preparation of 50:50 by Weight AMPS-Na/Sodium Methacrylate AMPS-Na Monomer Solution
Preparation Materials I. Compressed air
II. Water-deionized or distilled—8,000 g
III. Sodium Hydroxide—1,050 g
IV. AMPS-Reaction grade—5,424 g Procedures 1. Dissolve III in II
2. Cool to 25° C. While stirring and purging below the surface with I add IV, keeping the temperature at 25°-40° C.
3. Stir this solution at room temperature for 60 minutes or more, (at pH 9.0) purging with I.
4. Adjust the pH of the solution to 9.0 with 20% w aqueous AMPS solution.
5. Adjust the solution weight to 15,000 g. with water.
6. Pressure filter the solution to remove precipitated iron and other insolubles. This gives a 40% w AMPS-Na solution.

Polymerization

Materials

V. NaOH—701
VI. H2O—distilled or deionized—11800
VII. Methacrylic acid (contg. 250 ppm MEHQ)—1492
VIII. AMPS-Na solution—40% w—4688
IX. Purified nitrogen
X. Ammonium Persulfate—17.43 g.

Procedure

1. A 5-gal glass reactor, equipped with a stainless steel stirrer, gas inlet tube, thermometer and condenser, was charged with V and VI. Stir until V is dissolved.

2. Add VII with stirring.

3. Add VIII.

4. Adjust pH of solution to 7 with dry AMPS. This requires about 10-15 g. of AMPS.

5. Stir and heat to 60° C., purging below the surface with IX at 2.0 SCFH.

6. Stir at 60° C., purging with IX at 2 SCFH for an additional 30 minutes.

7. Add X (dissolved in 70 g. $H_2O$). Control temperature at 60°-62° with heating mantle and ice bath. The viscosity increased slowly and the reaction was mildly exothermic. The reaction was held at 60° under nitrogen for 6 hours.

8. Cool to room temperature.

9. Determine Brookfield viscosity using number 2 spindle at 6 rpm. It was 2400 cp.

CONTROLLED MONOMER ADDITION

The following observations and proposed techniques have been developed independent of the supplier of polymer material by the applicant of the present specification.

In the case of copolymerization of the AMPS monomer with other monomers, it has been observed that for the maximum benefit of the copolymer to be realized in regard to absorbency and other desired properties, the addition of the monomers to the copolymerization process must be controlled. In this respect, the varying polymerization rates of the monomers involved plays an important part in the composition of the final copolymer. For example, in the copolymerization of AMPS with acrylic acid, the polymerization rate of AMPS in the free acid state is so great that if the monomer and acrylic acid were mixed in water with a free radical initiator, the result would be immediate formation of AMPS homopolymer and possibly copolymer molecules very rich in AMPS content, followed by formation of copolymers very rich in acrylic acid content and acrylic acid homopolymers, with very little formation of copolymer molecules containing the exact or approximate desired ratio of AMPS to acrylic acid units. This effect is usually moderated to some extent by forming the sodium salt of the AMPS monomer, which has a slower rate of polymerization than the free acid form. However, the sodium AMPS still has a greater rate of polymerization than acrylic acid, resulting in the same uneven monomer distribution. Furthermore, if one makes the sodium salt of AMPS, it is usually more economical from a commercial standpoint to make the sodium salt of acrylic acid at the same time, resulting in an even wider monomer unit distribution among the resulting polymer molecules. This distribution is widened even more if an even slower polymerizing monomer such as methacrylic acid is substituted for acrylic acid. If a terpolymer of AMPS, acrylic acid, and methacrylic acid is desired, the distribution picture is even more complex. Therefore, in order to insure that the resulting copolymer molecules are indeed polymer chains consisting of the desired ratio of monomer units instead of a mixture of various homopolymers and copolymers, it has been found that careful attention must be given to the method of adding the various monomers to the copolymerization process in order to optimize the absorbency and other desired properties of the resulting fiber. This technique of controlling the monomer addition is well known to those skilled in the art and involves consideration of monomer reactivity ratios and other kinetic parameters associated with the particular monomer in question. For example, if one wanted a 50/50 by weight copolymer of sodium AMPS and sodium methacrylate, one would start the polymerization with a fraction of the total monomer amount in the water. This fraction would contain more than 50 percent by weight of the sodium methacrylate monomer and less than 50 percent of the sodium AMPS monomer. The remaining monomer, which is now in a ratio of greater than 50 percent sodium AMPS and less than 50 percent sodium methacrylate, can be added to the polymerization medium continuously, in one portion, or in several portions with ever increasing weight ratios of sodium AMPS to sodium methacrylate. The exact technique of controlling monomer addition can be first estimated by mathematical calculations based on the reactivity ratios or other kinetic parameters of the monomers involved and then modified by experience.

It will be apparent that this invention may take various forms which will nonetheless be within the substance herein disclosed.

What is claimed is:

1. A highly absorbent cellulosic fiber containing in a physical admixture with cellulose at least about 2% by weight based on the weight of the cellulose of a homopolymer consisting essentially of polymerized 2-acrylamido-2-methylpropane sulfonic acid monomers or the partial or complete alkali metal or ammonium salts thereof.

2. The fiber as in claim 1 in which said homopolymer is in the ratio of about 5 to 15 parts of said homopolymer to 100 parts of said cellulose.

3. The fiber as in claim 1 in which said sulfonic acid is in the sodium salt form.

4. The fiber as in claim 1 in which said homopolymer is in the ratio by weight of about 5 parts of said homopolymer to 100 parts of said cellulose.

5. The highly absorbent fiber of claim 1 prepared by adding from about 2% to about 35% by weight based on the weight of the cellulose of said homopolymer to the viscose solution from which said fiber is made.

6. The fiber as in claim 1 in which said homopolymer is in the ratio by weight of about 15 parts of said homopolymer to 100 parts of said cellulose.

7. A process for improving the fluid absorbency of a regenerated cellulose fiber, said process comprising spinning a spinnable viscose solution containing both cellulose and a homopolymer of 2-acrylamido-2-methylpropane sulfonic acid monomer or an alkali metal or ammonium salt thereof to form a regenerated cellulose fiber having at least 2% of said polymerization product or a salt thereof physically mixed with cellulose.

8. A highly absorbent cellulosic fiber containing in a physical admixture with cellulose at least about 2% by weight based on the weight of the cellulose of a copolymer comprising at least about 10% by weight of 2-acrylamido-2-methylpropane sulfonic acid monomers or the partial or complete alkali metal or ammonium salts thereof and at least one polymerizable, hydrophilic comonomer.

9. The fiber as in claim 8 wherein said comonomer is selected from the group consisting of acrylonitrile, acrylic acid and methacrylic acid.

10. The fiber as in claim 9 wherein said copolymer is in the ratio by weight of about 35–70 parts of said hydrophilic comonomer and 65–30 parts of said sulfonic acid monomer.

11. The fiber as in claim 10 in which said comonomer is acrylic acid.

12. The fiber as in claim 10 in which said comonomer is acrylonitrile.

13. The fiber as in claim 10 in which said sulfonic acid is in the sodium salt form.

14. The fiber as in claim 12 in which said comonomer is hydrolyzed with aqueous base to convert the nitrile groups to amide and/or acid groups.

15. The fiber of claim 10, in which said comonomer is, methacrylic acid.

16. The fiber as in claim 8 wherein said polymerizable, hydrophilic comonomer contains a functional group selected from the group consisting of carboxylic acid, hydroxyl, amide, ether, sulfonic acid and nitrile.

17. The fiber as in claim 8 wherein said copolymer comprises additionally at least one polymerizable insolubilizing reactive comonomer.

18. The fiber as in claim 17, wherein said reactive comonomer is selected from the group consisting essentially of N-methylol acrylamide, hydroxymethyl diacetone acrylamide, glycidyl methacrylate, hydroxyethyl acrylate, hydroxyethyl methacrylate, hydroxypropyl acrylate, hydroxypropyl methacrylate, and acrylamide.

19. The fibers in claim 8 in which said copolymer is in the ratio of about 5 to 15 parts of said copolymer to 100 parts of said cellulose.

20. The fiber as in claim 8 in which said copolymer is in the ratio by weight of about 5 parts of said copolymer to 100 parts of said cellulose.

21. The highly absorbent fiber of claim 8 prepared by adding from about 2% to about 35% by weight based on the weight of the cellulose of said copolymer to the viscose solution from which said fiber is made.

22. The fiber as in claim 8 in which said copolymer is in the ratio by weight of about 15 parts of said copolymer to 100 parts of said cellulose.

23. A highly absorbent cellulose fiber containing in a physical admixture with cellulose at least about 2% by weight based on the weight of the cellulose of a copolymer consisting essentially of at least about 10% by weight of 2-acrylamido-2-methylpropane sulfonic acid monomers or the partial or complete alkali metal or ammonium salts thereof and at least one hydrophilic polymerizable comonomer capable of reacting with cellulose or other functional groups in said copolymer so as to insolubilize said copolymer.

24. The fiber as in claim 23, in which said copolymer contains from about 10% to about 90% by weight of said sulfonic acid monomer.

25. The fiber as in claim 23, wherein said reactive comonomer is selected from the group consisting essentially of N-methylol acrylamide, hydroxyethyl diacetone acrylamide, glycidyl methacrylate, hydroxyethyl acrylate, hydroxyethyl methacrylate, hydroxypropyl acrylate, hydroxypropyl methacrylate, and acrylamide.

26. The fibers in claim 23, in which said copolymer is in the ratio of about 5 to 15 parts of said copolymer to 100 parts of said cellulose.

27. The highly absorbent fiber of claim 23, prepared by adding from about 2% to about 35% by weight based on the weight of the cellulose of said copolymer to the viscose solution from which said fiber is made.

28. A process for improving the fluid absorbency of a regenerated cellulose fiber, said process comprising spinning a spinnable viscose solution containing both cellulose and a copolymer comprising from about 10% to about 90% by weight of a 2-acrylamido-2-methylpropane sulfonic acid monomer or an alkali metal or ammonium salt thereof and at least one polymerizable, hydrophilic comonomer to form a regenerated cellulose fiber having at least 2% of said polymerization product or a salt thereof physically mixed with cellulose.

29. A process for improving the fluid absorbency of a regenerated cellulose fiber, said process comprising spinning a spinnable viscose solution containing both cellulose and a copolymer consisting essentially of at least about 10% by weight of a 2-acrylamido-2-methylpropane sulfonic acid monomer or an alkali metal or ammonium salt thereof and a hydrophilic polymerizable insolubilizing reactive comonomer to form a regenerated cellulose fiber having at least 2% of said polymerization product or a salt thereof physically mixed with cellulose.

* * * * *